(12) United States Patent
Hasenoehrl et al.

(10) Patent No.: US 10,561,754 B2
(45) Date of Patent: *Feb. 18, 2020

(54) VOLATILE COMPOSITION DISPENSER WITH LOCKABLE BUTTON

(71) Applicant: The Procter & Gamble Company, Cincinnati, OH (US)

(72) Inventors: Erik John Hasenoehrl, Loveland, OH (US); Rahul Vyas, Singapore (IN); Stefano Deflorian, Trento (IT); Walter Sordo, Trento (IT); Stefano Baldessari, Caldonazzo (IT); Ricard Tomas Vilarrasa, Trento (IT)

(73) Assignee: The Procter & Gamble Company, Cincinnati, OH (US)

( * ) Notice: Subject to any disclaimer, the term of this patent is extended or adjusted under 35 U.S.C. 154(b) by 150 days.

This patent is subject to a terminal disclaimer.

(21) Appl. No.: 15/582,828

(22) Filed: May 1, 2017

(65) Prior Publication Data

US 2017/0319731 A1 Nov. 9, 2017

Related U.S. Application Data

(60) Provisional application No. 62/330,865, filed on May 3, 2016.

(51) Int. Cl.
*A61L 9/12* (2006.01)
*B05B 12/00* (2018.01)
*A01M 1/20* (2006.01)

(52) U.S. Cl.
CPC ............. *A61L 9/12* (2013.01); *A01M 1/2044* (2013.01); *A61L 9/127* (2013.01);
(Continued)

(58) Field of Classification Search
CPC ........ A61L 9/12–9/127; A61L 2209/13; A61L 2209/131; A61L 2209/133; A61L 2209/134; A01M 1/2044; A01M 1/2055
(Continued)

(56) References Cited

U.S. PATENT DOCUMENTS 4,382,548 A * 5/1983 van der Heijden ....... A61L 9/12
                                                          220/282
4,572,375 A * 2/1986 Baer ........................ A61L 9/12
                                                          206/524.1
(Continued)

FOREIGN PATENT DOCUMENTS

WO  WO 98/16262 A1   4/1998
WO  WO 2006/061802 A1   6/2006

OTHER PUBLICATIONS

PCT Search Report PCT/US2017/030713; dated Jul. 26, 2017; 13 Pages.
(Continued)

*Primary Examiner* — Cody J Lieuwen
(74) *Attorney, Agent, or Firm* — Abbey A. Lopez

(57) ABSTRACT

There is a volatile composition dispenser comprising a housing comprising a rear frame having a frame opening, and an inner wall. A push button is movably disposed in the frame opening and the inner wall and is configured to be movable with respect to the inner wall from a first position to a second position wherein the push button is interlocked with the inner wall in the second position.

9 Claims, 10 Drawing Sheets

(52) U.S. Cl.
CPC ..... B05B 12/0022 (2018.08); *A61L 2209/131* (2013.01); *A61L 2209/133* (2013.01)

(58) Field of Classification Search
USPC ..................................................... 239/34–60
See application file for complete search history.

(56) References Cited

U.S. PATENT DOCUMENTS

| | | | | |
|---|---|---|---|---|
| 8,622,209 | B2 * | 1/2014 | Isaac | B65D 81/32 206/222 |
| 8,740,110 | B2 | 6/2014 | Gruenbacher et al. | |
| 8,931,711 | B2 | 1/2015 | Gruenbacher et al. | |
| 9,015,989 | B1 * | 4/2015 | Zeamer | A01M 1/2005 239/37 |
| 9,439,993 | B2 | 9/2016 | Gruenbacher et al. | |
| 2006/0191189 | A1 * | 8/2006 | Mayo | A01M 1/2005 43/131 |
| 2010/0314461 | A1 * | 12/2010 | Gruenbacher | A61L 9/12 239/6 |
| 2011/0180621 | A1 | 7/2011 | Gruenbacher et al. | |
| 2014/0110495 | A1 * | 4/2014 | Gundy | A61L 9/12 239/44 |
| 2015/0060565 | A1 | 3/2015 | Furner | |
| 2016/0354505 | A1 | 12/2016 | Gruenbacher et al. | |
| 2017/0043047 | A1 | 2/2017 | Beck et al. | |

OTHER PUBLICATIONS

PCT Search Report PCT/US2017/030715; dated Jul. 26, 2017; 14 Pages.
PCT Search Report PCT/US2017/030716; dated Jul. 20, 2017; 13 Pages.
PCT Search Report PCT/US2017/030717; dated Sep. 11, 2017; 15 Pages.
U.S. Appl. No. 15/582,834, filed May 1, 2017, Hasenoehrl, et al.
U.S. Appl. No. 15/582,841, filed May 1, 2017, Hu, et al.
U.S. Appl. No. 15/582,849, filed May 1, 2017, Deflorian, et al.
All Office Actions for U.S. Appl. No. 15/582,834.
All Office Actions for U.S. Appl. No. 15/582,841.
All Office Actions for U.S. Appl. No. 15/582,849.

* cited by examiner

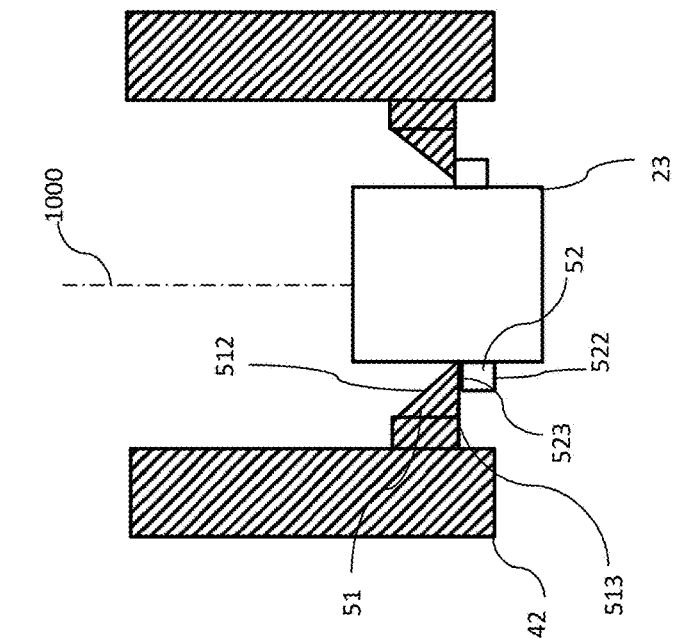
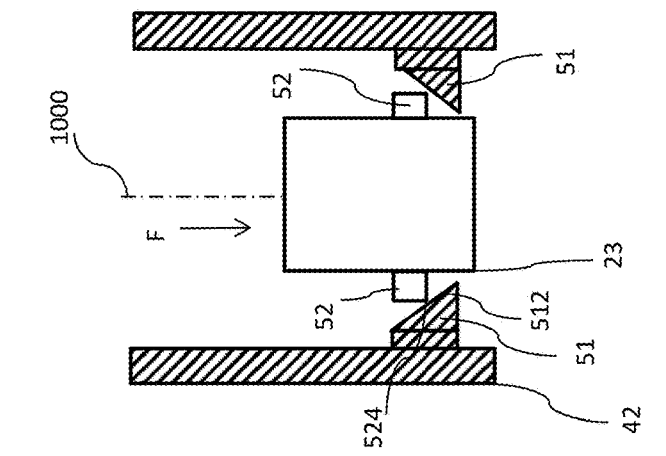
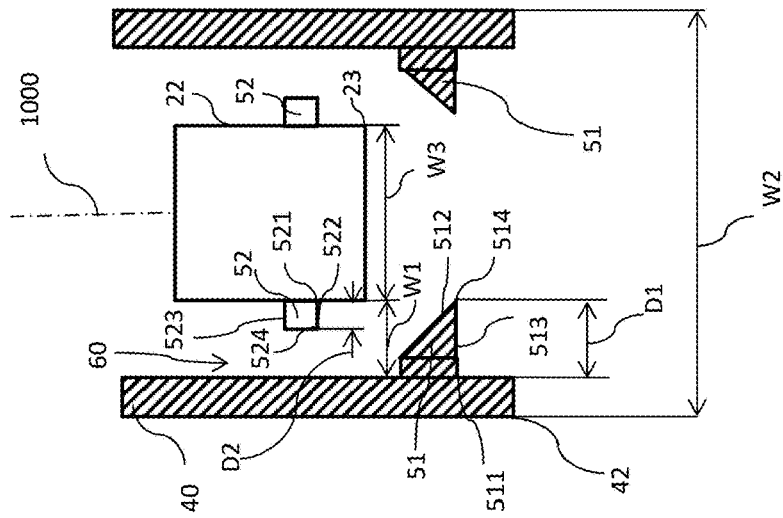
FIG. 6A
FIG. 6B
FIG. 6C

VOLATILE COMPOSITION DISPENSER WITH LOCKABLE BUTTON

FIELD OF THE INVENTION

The invention relates to the field of devices and systems for delivering a volatile composition and particularly relates to a volatile composition dispenser with a lockable push button, and a method of locking a push button within a housing of a volatile composition dispenser.

BACKGROUND OF THE INVENTION

Systems for delivering volatile materials to the atmosphere are well known in the art, and include for example, insect repellants, air fresheners, malodor removal agents. Such systems function by evaporating a volatile material through a medium such as a permeable membrane into a space to deliver a variety of benefits such as air freshening or malodor removal or a combination thereof. Typically, the volatile composition is stored in a sealed container that is opened or punctured to release the volatile composition to the air.

PCT Publication No. WO 98/16262 (hereinafter, "WO98/16262") describes a disposable air freshener dispenser device having a push-button actuator which can be manually operated to initiate the dispensing of air freshener composition into the atmosphere. The device of WO98/16262 has an air freshener medium within a container, and a push button actuator which can be manually operated to rupture a foil covering the container for initiating the dispensing of the air freshener into the atmosphere. A problem associated with such devices is that it is difficult for a user (such as a consumer) to determine whether the air freshener device is activated until the consumer smells the air freshener composition. As a result, if the consumer does not smell the air freshener composition, the consumer may consider that the device is not activated or is malfunctioning and this leads to reduced consumer satisfaction. Another problem of the prior art device is it is not easily detected by other users (such as retail store owners) whether such devices have been tampered with or inadvertently activated during handling or transportation to the retail stores. This may result in defective air freshener devices being displayed for sale which inevitably lead to consumer complaints when consumers purchase a defective air freshener device.

Therefore, there exists a need for an apparatus for delivering a volatile material that can be manually operated and provides a signal to users indicating activation of the apparatus at the same time.

SUMMARY OF THE INVENTION

In order to address the above-identified needs, the present invention provides a volatile composition dispenser comprising:
a) a housing comprising a rear frame wherein the rear frame comprises a frame opening having a longitudinal axis;
b) an inner wall in the opening, the inner wall comprising a proximal end at a periphery of the opening and a distal end;
c) a button configured to be movable within the frame opening from a first position to a second position relative to the distal end of the inner wall, wherein the button comprises a button body;
d) at least one first protrusion located at the distal end of the inner wall;
e) at least one second protrusion disposed on the button body wherein the second protrusion is aligned to engage with and move past the first protrusion as the button is moved from the first position to the second position wherein the second protrusion is below the first protrusion relative to the distal end of the inner wall in a vertical direction parallel to the longitudinal axis to prevent return of the button to the first position; and
f) a volatile composition cartridge disposed within the housing adjacent the button.

By having the second protrusion on the button configured to engage and move past the first protrusion on the inner wall after activation of the button, the advantage is the second protrusion on the button cannot return to the first position. As a result, the button is retained in a depressed position, and the difference in positions of the button along the longitudinal axis or a vertical direction gives the user a visual signal that the dispenser is activated.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

FIGS. 6A-6C are schematic drawings which depict the movement of the button of FIG. 5 within the rear frame of FIG. 4;

DETAILED DESCRIPTION OF THE INVENTION

The present invention relates to a volatile composition dispenser for the delivery of a volatile material to the atmosphere. The dispenser is suitable for purposes of providing fragrances, air fresheners, deodorizers, odor eliminators, malodor counteractants, insecticides, insect repellants, medicinal substances, disinfectants, sanitizers, mood enhancers, aromatherapy aids, or for any other purpose using a volatile material or a volatile composition that acts to condition, modify, or otherwise change the atmosphere or the environment. For the purposes of illustrating the present invention in detail, but without intending to limit the scope of the invention, the invention will be described in a volatile composition dispenser for delivering a liquid composition containing perfume, perfume ingredients and or perfume raw materials.

Figure 1:
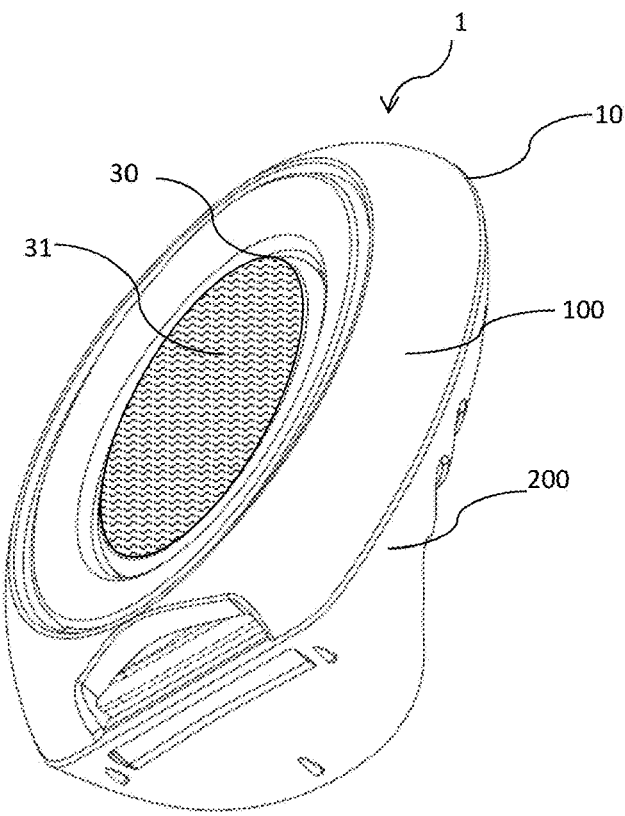
FIG. 1 is a front perspective view of a volatile composition dispenser according to an embodiment.
Figure 2:
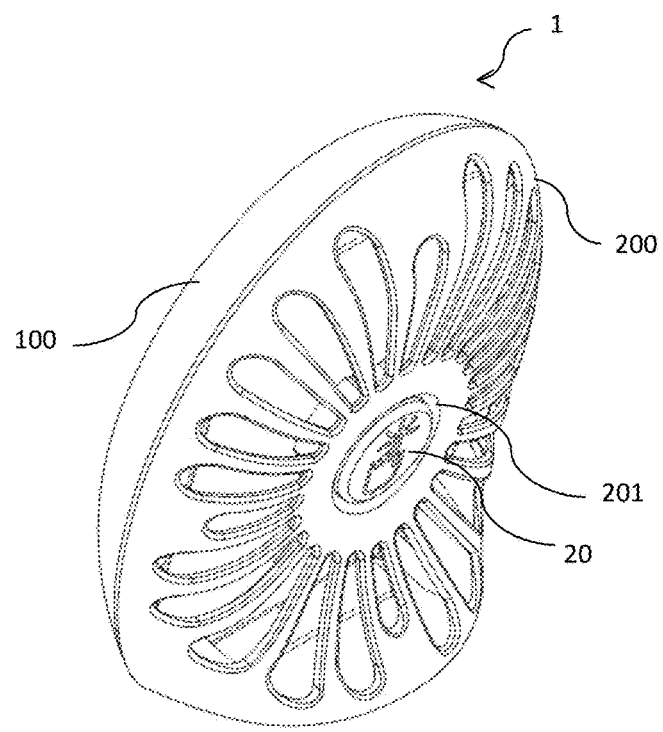
FIG. 2 is a rear perspective view of the volatile composition dispenser shown in FIG. 1.

FIG. 1 shows a front perspective view of a volatile composition dispenser 1 (hereinafter "dispenser") according to the present invention and FIG. 2 shows a rear perspective view of the dispenser 1. The dispenser 1 comprises a housing 10 having a front cover 100 and a rear frame 200, the front cover 100 and the rear frame 200 defining an interior space. The rear frame 200 is provided with a frame opening 201 (hereinafter "opening") located substantially in the centre of the rear frame 200. A push button 20 (hereinafter "button") is disposed within the opening 201 and is movable with respect to the rear frame 200 for enabling a user to activate the dispenser 1. A cartridge 30 containing a volatile composition 31 is located within the housing 10.

Figure 3:
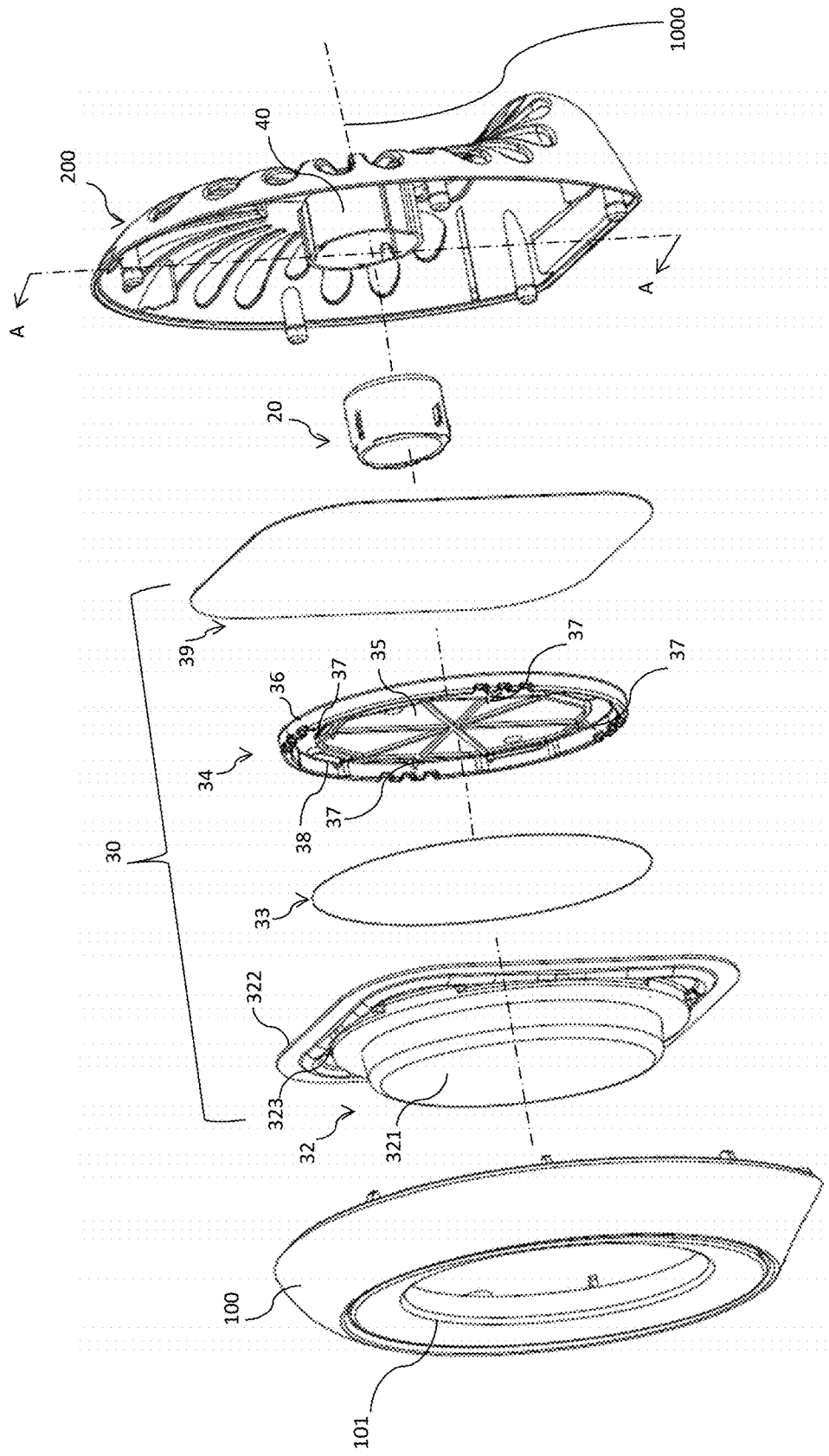
FIG. 3 is a side perspective exploded view of the volatile composition dispenser shown in FIG. 1.

FIG. 3 shows internal components of the dispenser 1. The front cover 100 comprises a window 101 configured for displaying the cartridge 30. The cartridge 30 comprises a container 32 having an orifice 321, within which the volatile composition 31 (as shown in FIG. 1) is stored. A rupturable substrate 33 is sealably attached to and covers the orifice 321 defining a reservoir to prevent the volatile composition 31 from being released until the dispenser 1 is activated. The rupturable substrate 33 may be ruptured to release the volatile composition 31 by actuating a rupture mechanism 34 positioned adjacent to the rupturable substrate 33. The rupture mechanism 34 comprises a movable member 35 movably attached to an outer frame 36 by a resilient member 38. The resilient member 38 may be formed of one or more springs 38. One or more rupture elements 37 are arranged within the rupture mechanism 34 to puncture holes in the rupturable substrate 33. The rupture element 37 may be a pin. The cartridge 30 may comprise a membrane 39 located on the exterior of the cartridge 30. The membrane 39 may be sealably attached to a flange 322 located at a periphery 323 of the container 32. The membrane 39 encloses the container 32, the volatile composition 31, the rupturable substrate 33, and the rupture mechanism 34. The membrane 39 may be configured to flex when a pressure or an actuation force is applied on the membrane 39.

To activate the dispenser 1, a user depresses the button 20 until it makes contact with the rupture mechanism 34 (through the membrane 39), and the pins 37 on the rupture mechanism 34 pierce the rupturable substrate 33. Once the rupturable substrate 33 is pierced, the volatile composition 31 flows out of the container 32, wets the membrane 39 and is then delivered to the atmosphere surroundings through evaporation from the membrane 39.

According to an embodiment of the present invention, the button 20 and the rear frame 200 are configured to enable efficient and controlled rupturing of the rupturable substrate 33 in the cartridge 30 while additionally providing a tactile and intuitive user experience to the user for activating the dispenser 1.

Figure 4:
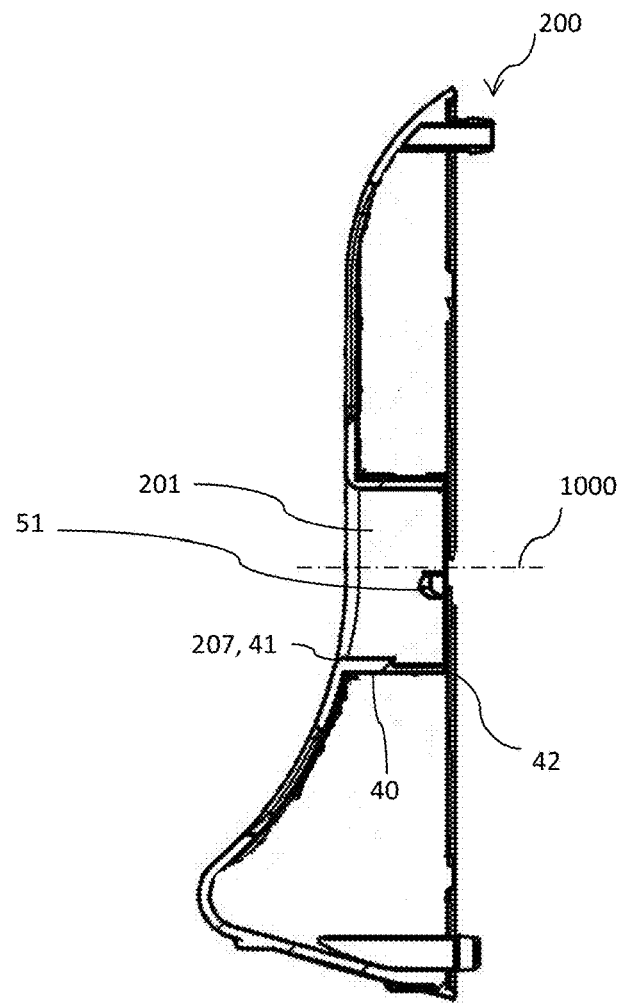
FIG. 4 is a side section view of the rear frame of FIG. 3 at section line A-A.

FIG. 4 shows a side section view A-A of the rear frame 200. An inner wall 40 is provided at a periphery 207 of the opening 201 and extends into the housing 10 from the interior of the rear frame 200. The inner wall 40 has a proximal end 41 flush with the periphery 207 of the opening 201, and a distal end 42 protruding into the housing 10. In the embodiment shown in FIG. 4, the inner wall 40 is solid and tubular in shape. However, the inner wall 40 may take some other shape such as for example a square cross section or a rectangular cross section. The inner wall 40 may be substantially cylindrical and comprise a continuous wall, or a segmented wall such as for example, a lattice structure or multiple elongate struts connected to one another. The inner wall 40 may define an extension of the opening 201 into the housing 10 with a central longitudinal axis 1000 running through the centre of the opening 201 and along which the button 20 can be depressed. Alternatively, the inner wall 40 may protrude out of the housing 10 such that the inner wall 40 defines an extension of the opening 201 out of the housing 10. Accordingly, the distal end 42 may be flush with the periphery 207 of the opening 201 and the proximal end 41 may protrude out of the housing 10.

Figure 5:
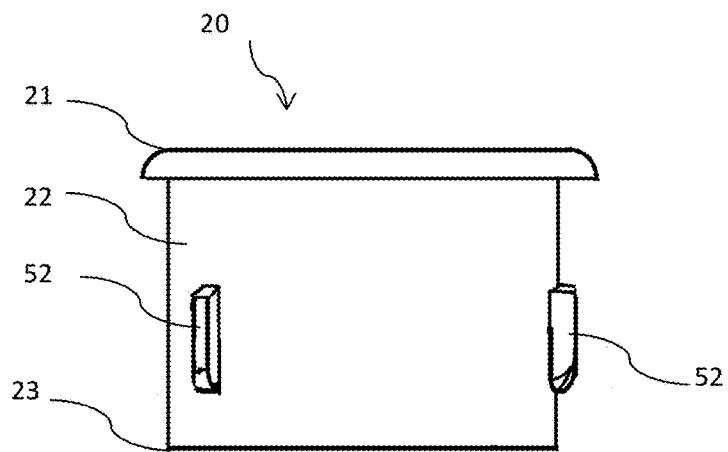
FIG. 5 is a front view of a button for a volatile composition dispenser according to an embodiment.

FIG. 5 is a front section view of the button 20 configured to fit and to move within the opening 201 of the rear frame 200. The button 20 comprises a top 21 and a button body 22 extending from the top 21 into the housing 10. In an embodiment, the top 21 is located in line with the periphery 207 of the opening 201 when the button 20 is in an "at rest" position (see for example FIG. 14A). Alternatively, the top 21 of the button 20 may protrude out of the opening 201 when "at rest" (see for example. FIG. 15A). The button body 22 extends substantially in parallel to the inner wall 40. Therefore the button body 22 may also have a tubular shape. One or more protrusions 50 extend from the button body 22 to define snap fits for assembling the button 20 to the inner wall 40.

Further, the dispenser 1 comprises an interlocking mechanism for preventing motion of the button 20 with respect to the rear frame 200 after activation of the dispenser 1. For example, the interlocking mechanism may comprise a snap-fit or interlocking joint. In embodiments, the interlocking mechanism may comprise structural features integral with the button 20 or the inner wall 40 such as hooks or protrusions on the button 20 which, after depression of the button, engage with corresponding undercuts, detents, protrusions, or openings in the inner wall 40 to lock the button 20 to the inner wall 40. In this way, the button 20 may not be released from the post-activation position without forced failure of the interlocking mechanism or the joint.

The interlocking mechanism may comprise at least one protrusion 51, 52 located on each of the inner wall 40 and the button body 22, aligned with one another such that they make contact as the button 20 is depressed. As shown in FIG. 4, the first protrusion 51 may be located at the distal end 42 of the inner wall 40. As shown in FIG. 5, a second protrusion 52 may be located proximate a distal end 23 of the button body 22. The first protrusion 51 and the second protrusion 52 may be generally elongate and extend in a direction parallel to the longitudinal axis 1000 of the opening 201.

FIG. 6A is a schematic drawing of the button 20 mounted within the rear frame 200 wherein the button 20 is in a "at rest" position. FIGS. 6B and 6C are schematic drawings depicting the movement of the button 20 between the "at rest" position to a post-activation position. The button 20 is configured to move linearly with respect to the rear frame 200, i.e. a straight push button that moves in a direction generally parallel to the longitudinal axis 1000 of the frame opening 201 upon depression of the button 20. Only the inner wall 40 and the button body 22 are shown to better illustrate the arrangement and movement of the button 20 relative to the inner wall 40.

The first and second protrusions 51, 52 are arranged within a gap 60 between the button body 22 and the inner wall 40 and are aligned to engage with one another in the plane generally parallel to the longitudinal axis 1000 of the frame opening 201. The size of the gap 60 may be uniform and constant along the longitudinal direction (length) of the button body 22. The gap 60 may comprise a first gap width (W1) between respective bases 511, 521 of the first and second protrusions 51, 52. Specifically, W1 is less than a sum of a depth (D1) of the first protrusion 51 relative to the inner wall 40 and a depth (D2) of the second protrusion 52 relative to the button body 22, and may be represented by the following formula:

$$W1 < D1 + D2$$

The first gap width, W1 is configured to enable the first and second protrusions 51, 52 to be engaged while enabling free movement of the button 20 prior to locking of the button 20 within the rear frame 200. The protrusion depth, D1 of the first protrusion 51 may be in the range of 1% to 2% of a width, W2 of the inner wall 40. The protrusion depth D2 of the second protrusion 52 may be in the range of 1% to 2% of a width, W3 of the button body 22. An advantage of the above ranges of the protrusion depth D1 of the first protrusion 51 and the protrusion depth D2 of the second protrusion 52 is to enable the user to receive a tactile feedback which provides a perception to the user that the dispenser is activated.

Referring to FIG. 6A, at least one of the first and second protrusions 51, 52 may be asymmetrical along its length, with a first surface 512, 522 facing the other of the first and second protrusions 51, 52 (when in a rest position) and a second surface 513, 523 facing away from the other of the first and second protrusions 51, 52. In an embodiment, as shown in FIG. 6A, a tip 514 is positioned between the first surface 512 and the second surface 513 of the first protrusion 51. The second protrusion 52 may have a symmetrical, or substantially symmetrical, form with, for example, a tip 524 for engaging the first surface 512 of the first protrusion 51.

In the at rest position (FIG. 6A), the first and second protrusions 51, 52 are spaced apart such as for example, the distal end 23 of the button body 22 may be proximal to the distal end 42 of the inner wall 40. Upon activation of the dispenser 1 through a force F applied on the button 20, the button 20 is depressed and, as the button 20 moves relative to the inner wall 40, the first and second protrusions 51, 52 make contact (as shown in FIG. 6B) through engagement of the tip 524 of the second protrusion 52 with the first surface 512 of the first protrusion 51. The first and second protrusions 51, 52 move past one another until the second protrusion 52 (on the button body 22) is proximal to the distal end 42 of the inner wall 40 (as shown in FIG. 6C). The second protrusion 52 may be below the first protrusion 51 in a vertical direction parallel to the longitudinal axis 1000. Alternatively, the second surfaces 513, 523 of the first and second protrusions 51, 52 may be adjacent to each other in the post activation position.

Figure 7:
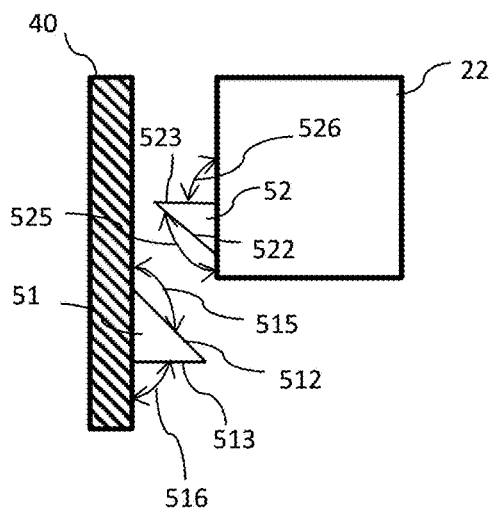
FIGS. 7 to 9 are schematic views showing different geometry configurations of first and second protrusions for the dispenser.
Figure 8:
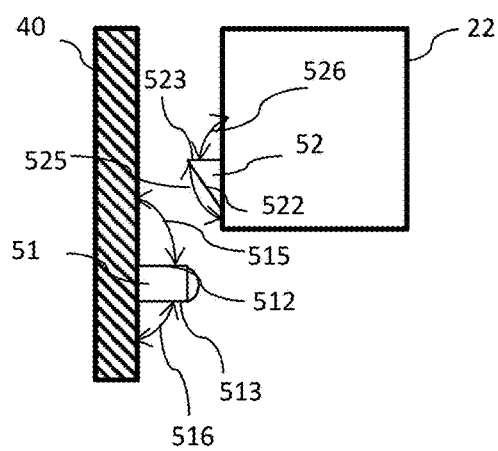
Figure 9:
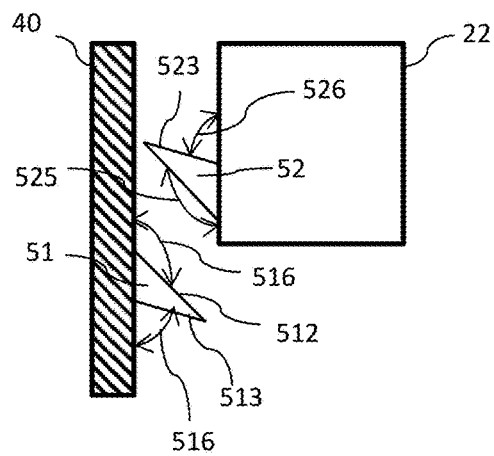

FIGS. 7 to 9 are schematic drawings showing variations in the geometry of the first and second protrusions 51, 52 for locking the button 20 to the rear frame 200 upon depression of the button 30. An angle 515, 525 of the first surfaces 512, 522 and an angle 516, 526 of the second surfaces 513, 523 relative to respectively the inner wall 40 or button body 22 may be different.

Further, for example as shown in FIG. 7, the angle 515 of the first surface 512 relative to the inner wall 40 may be greater than the angle 516 of the second surface 513 relative to the inner wall 40. The angle 515, 525 of the first surface 512, 522 of one or both of the first or second protrusions 51, 52 may be between 80° and 150°, whereas the angle 516, 526 of the second surface 513, 523 of one or both of the first and second protrusions 51, 52 is between 5° and 80°.

By providing an obtuse angle for the angle 515, 525 of the first surface 512, 522, it is easier for the two protrusions 51, 52 to pass one another during activation, whereas the more acute angle for the angle 516, 526 of the second surface 513, 523 makes it difficult for the protrusions 51, 52 to pass after activation. Therefore, once the button 20 has been depressed and the protrusions 51, 52 move past one another, the button 20 is prevented from returning to its original position.

Alternatively, as shown in FIG. 8, only one of the protrusions 51, 52 has an assymetrical form, whereas the other protrusion 51, 52 may have a symmetrical, or substantially symmetrical, form with, for example, a rounded tip.

Further, referring to FIG. 9, at least the second surfaces 513, 523 of both the first and second protrusions 51, 52 may have corresponding angles relative respectively to the inner wall 40 and button body 22 such that following activation, the protrusions 51, 52 lock together. For example, the angle 516, 526 of the second surfaces 513, 523 of both the first and second protrusions 51, 52 may be between 90° and 150°.

The different angles of the first surfaces 512, 522, and second surfaces 513, 523 result in the button body 22 flexing and snapping into place after the first and second protrusions 51, 52 have moved past one another thereby providing the user with a clear intuitive signal (and preferably an audible click).

Depending on an elastic property of either one of the first protrusion 51 or the second protrusion 52, one of the first protrusion 51 and the second protrusion 52 may be configured to deflect to enable the second protrusion 52 to move past the first protrusion 51 into a second position as shown in FIG. 6C. Further, the second protrusion 52 of the button 20 may be configured to be rigid to transmit the force exerted by the user on the button 20 to rupture the rupturable substrate 33 in the cartridge 30. Still further, the second protrusion 52 may be configured to be resilient to generate a clicking sound when the second protrusion 52 contacts the first protrusion 51 after it moves past the first protrusion 51.

Figure 10:
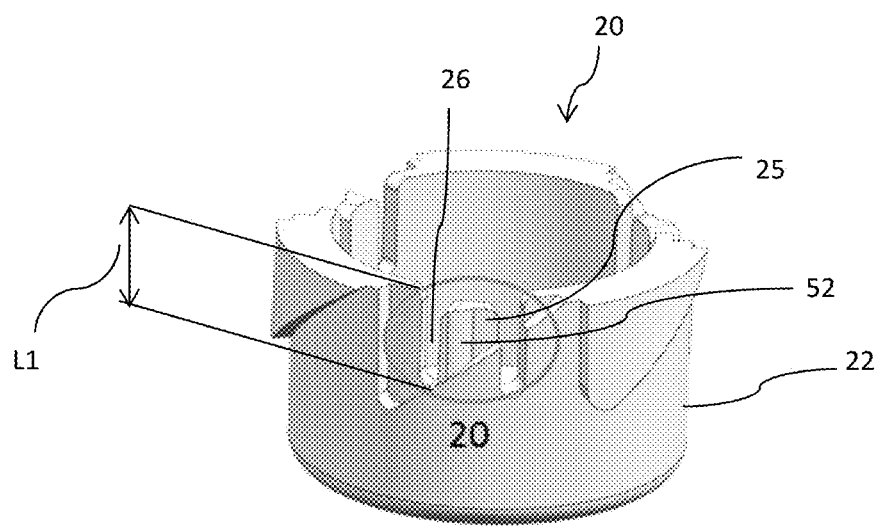
FIG. 10 is a perspective view of a button for a volatile composition dispenser according to an embodiment.

Referring to FIG. 10, the button body 22 may be formed of a plurality of flexible wall sections 25 wherein the second protrusion 52 is disposed on a flexible wall section 25. The flexible wall sections 25 are configured to flex by forming channels 26 in the button body 22 adjacent to the second protrusions 52. Each channel 26 may comprise a length L1 substantially parallel to the longitudinal axis 1000 and configured to make the wall section 25 flexible for ease of activation. At least one channel 26 may define a substantially U-shape. Another advantage of having the second protrusions 52 disposed on the flexible wall sections 25 is that to avoid plastic deformations on the first protrusions 51 and the second protrusions 52. Further, upon activation of the button 20, the flexing of the flexible wall sections 25 to contact the inner wall 40 generates a click sound and a tactile feeling is provided to the user thereby providing audible and tactile signals at the same time indicating that the dispenser 1 is activated.

Figure 11:
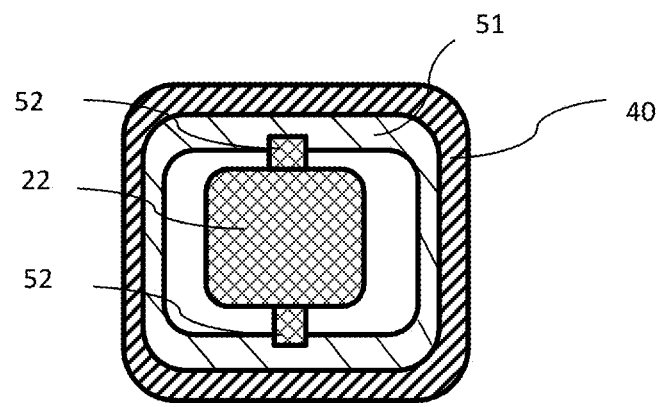
FIG. 11 is a schematic drawing of an alternative embodiment of first and second protrusions for the dispenser.

Referring to FIG. 11, the first protrusion 51 may be a continuous lip extending circumferentially around the inner wall 40 wherein the second protrusion 52 of the button 20 is aligned for engaging and moving past the first protrusion 51.

As shown in FIGS. 6A to 6C, the protrusions 51, 52 are configured for a straight push button within a rear frame. However, it will be appreciated that alternative designs and arrangements of the first protrusion 51 and the second protrusion 52 to enable a lockable button may be configured depending on a desired actuation of a button 20 within a rear frame 200. Such alternative designs will be described later in the following description with reference to FIG. 12.

Figure 12:
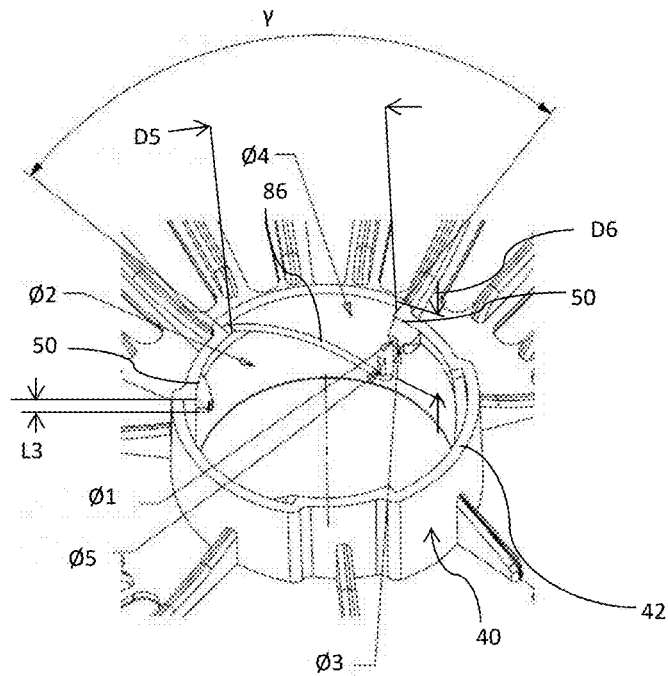
FIG. 12 is a partial perspective view of a rear frame for a volatile composition dispenser.
Figures 13A, 13B:
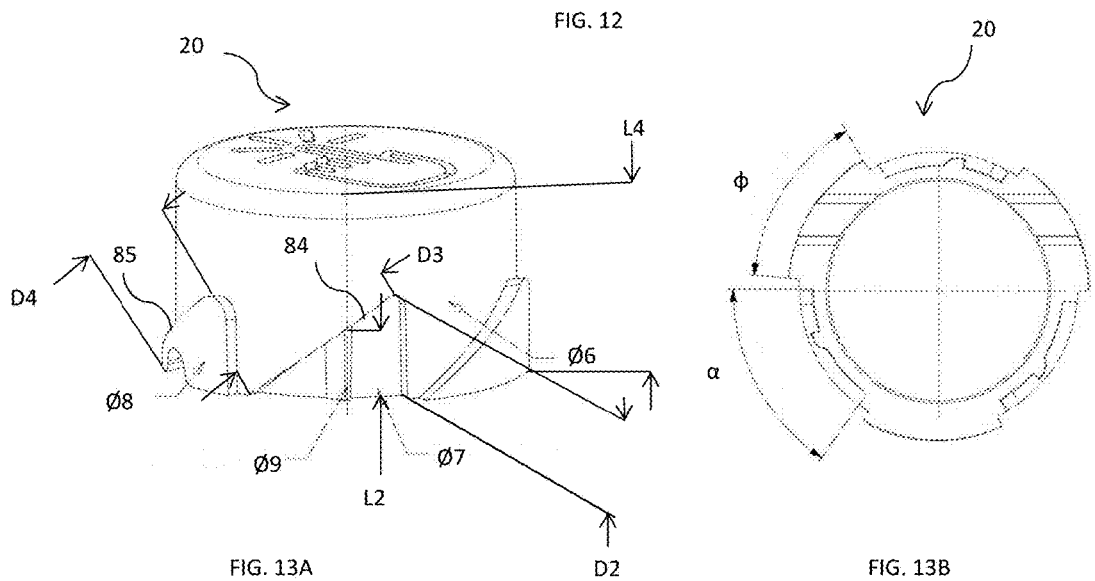
FIG. 13A is a perspective view of a button for a volatile composition dispenser.
FIG. 13B is a bottom view of the button of FIG. 13A.

FIG. 12 is a perspective view of the rear frame 200 of FIG. 3 (partially shown), FIG. 13A is a perspective view of the button 20 and FIG. 13B is a bottom view of the button 20. The first protrusion 51 or the second protrusion 52 may be generally elongate and extend in a direction parallel to the longitudinal axis 2000 of the frame opening 201. Each of the second protrusions 52 may comprise a length, L2 and each of the first protrusions 51 may comprise a length, L3. Each of the lengths L2 and L3 may be in the range of 7% to 20% of a length (L4) of the button 20.

One or more second protrusions 52 may be disposed on a cam guide 80 for engaging the one or more first protrusions 51 during rotation of the button 20. The first protrusions 51 are disposed at the distal end 42 of the inner wall 40 wherein the first protrusion 51 is aligned for engaging the cam guide 80 of the button body 22. The cam guide 80 may comprise a plurality of first cam tracks 84 formed on the button body 22. The first cam tracks 84 are radially spaced apart on the button body 22 for engaging the first protrusions 51 on the distal end 42 of the inner wall 40. The cam guide 80 may further comprise a plurality of second cam tracks 85 intermediate the first cam tracks 84.

Figure 17A:
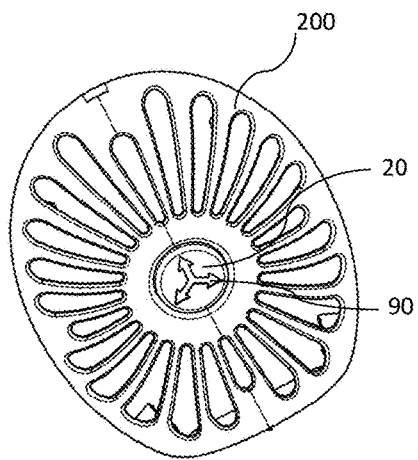
FIG. 17A is a rear perspective view of a volatile composition dispenser with a button in a first position before activation.
Figure 17B:
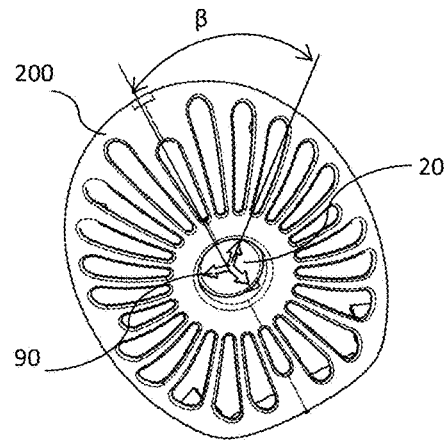
FIG. 17B is a rear perspective view of the button of FIG. 17A in a second position after activation.

A cam angle α of the cam guide 80 may be configured to obtain a desired button stroke S (mm) and a rotation angle β of the button 20 about the longitudinal axis 1000 and/or the cylindrical axis 2000 (shown in FIG. 17B). The desired button stroke may be a distance to be travelled by the button 20 along the longitudinal axis 1000 of the opening 201 in order to cause the rupture elements 37 of the rupture mechanism 34 to puncture the substrate 33.

By having the cam guide 80 and the first protrusion 51 cooperating to move the button 20 axially along and rotate about the longitudinal axis 1000 in a clockwise or an anti-clockwise direction, the top 21 of the button 20 may have different orientations with respect to the rear frame 200 as shown in FIG. 17A and FIG. 17B.

Specifically, the second cam tracks 85 extend radially outward from and spaced circumferentially on the button body 22 and arranged to engage mating cam track 86 formed on the inner wall 40 upon insertion of the button 20 in the inner wall 40. In an embodiment, each second cam track 85 and a mating cam track 86 may be configured to correspond in shape or profile to the first step 84 so as to define a continuous cam profile for rotation of the button 20 about the longitudinal axis 1000 and axial movement of the button 20 along the longitudinal axis 1000.

Figure 18A:
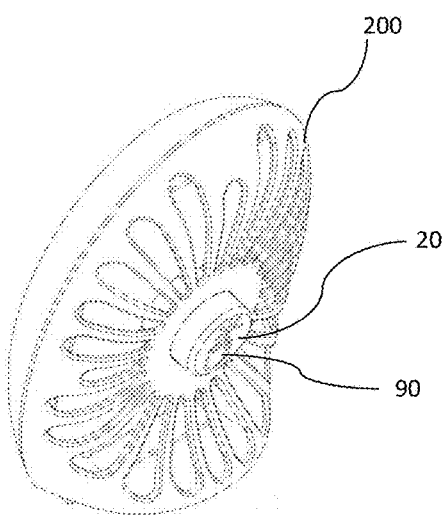
FIG. 18A is a rear perspective view of a volatile composition dispenser with a button positioned above a periphery of an opening in a rear frame in a first position before activation.
Figure 18B:
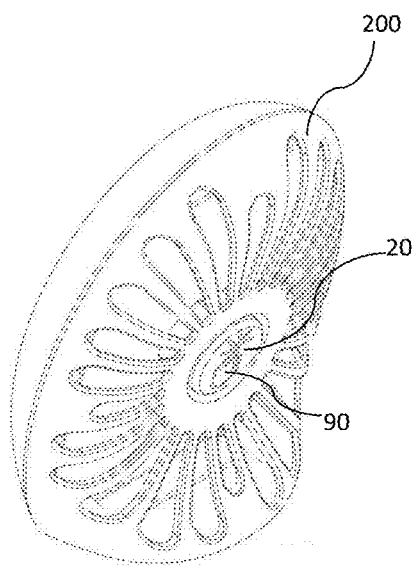
FIG. 18B is a rear perspective view of the button of FIG. 18A in a second position after activation.

Further, the second cam tracks 85 and the mating cam tracks 86 may be configured to allow the button 20 to be arranged within the frame 200 at a height relative to the distal end 42 of the inner wall 40. The height may be varied so that upon assembly, the button 20 may be either flush with the periphery 207 of the opening 201 in the first position (as shown in FIG. 17A) or extending above the periphery 207 of the opening 201 in the first position (as shown in FIG. 18A).

In embodiments, such as shown in FIGS. 17A, 17B, 18A, 18B, indicia 90 may be disposed on the top 21 of the button 20 to provide a signal to a user of the dispenser 1. For example, referring to FIG. 17A, the indicia 90 may include a graphical representation like hands of a clock to show the button 20 in one orientation relative to the periphery of the opening in the first position and in a different orientation in the second position. Alternatively, referring to FIG. 18A, the indicia 90 may be a graphical symbol indicating a position for actuating the button 20 or activating the dispenser 1.

Figure 14A:
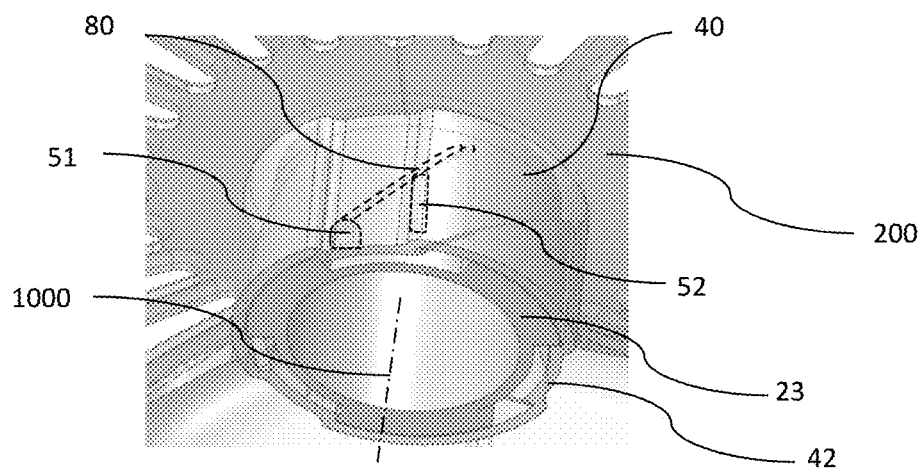
FIG. 14A to 14C are interior perspective views of the button of FIG. 13A within the rear frame of FIG. 12 which depict movement of the button.
Figure 14B:
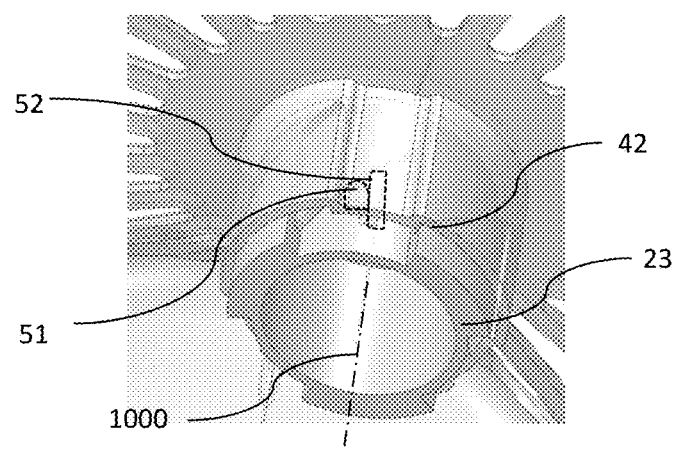
Figure 14C:
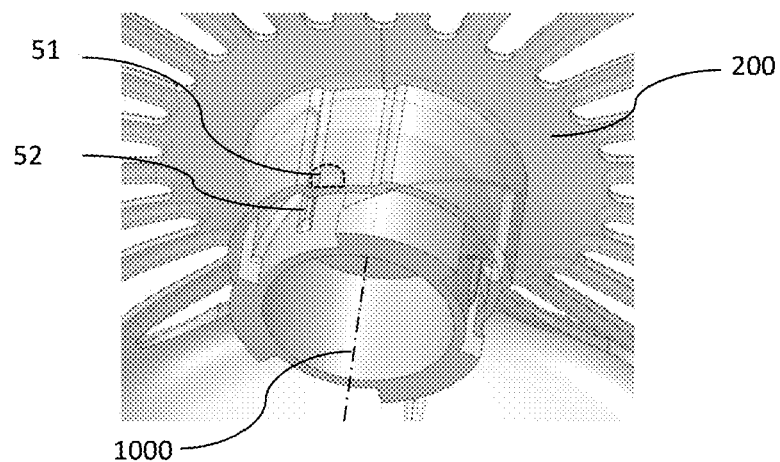

FIG. 14A is a partial perspective view of the button 20 mounted within the rear frame 200 wherein the button 20 is in a "at rest" position. FIGS. 14B and 14C are cross-sectional views depicting the movement of the button 20 between the "at rest" position to a post-activation position.

In FIG. 14A, as no force is being applied to the button 20, the button 20 is in the rest position ("first position"). In the first position, a first protrusion 51 (shown in broken lines) engages the cam guide 80 (broken lines on the button body 22) and is aligned with the distal end 23 of the button 20. Upon activation of the dispenser, the button 20 is moved into the housing (10) and, as the first protrusion 51 and the cam guide 80 engage throughout the movement of the button 20 (as shown in FIG. 14B), the button 20 rotates and moves axially along the longitudinal axis 1000 until the distal end 23 of the button 20 extends into the housing 10 of FIG. 1 and is spaced apart from and below the distal end 42 of the inner wall 40 (as shown in FIG. 14C). In an embodiment, the distal end 23 of the button 20 may be below the first protrusion 51 in a vertical direction parallel to the longitudinal axis 1000. To ensure that the button 20 is maintained in the post-activation position of FIG. 14C, L2 is greater than L3 Still further, L3 may be in the range of 1% to 55% of L2.

Figure 15:
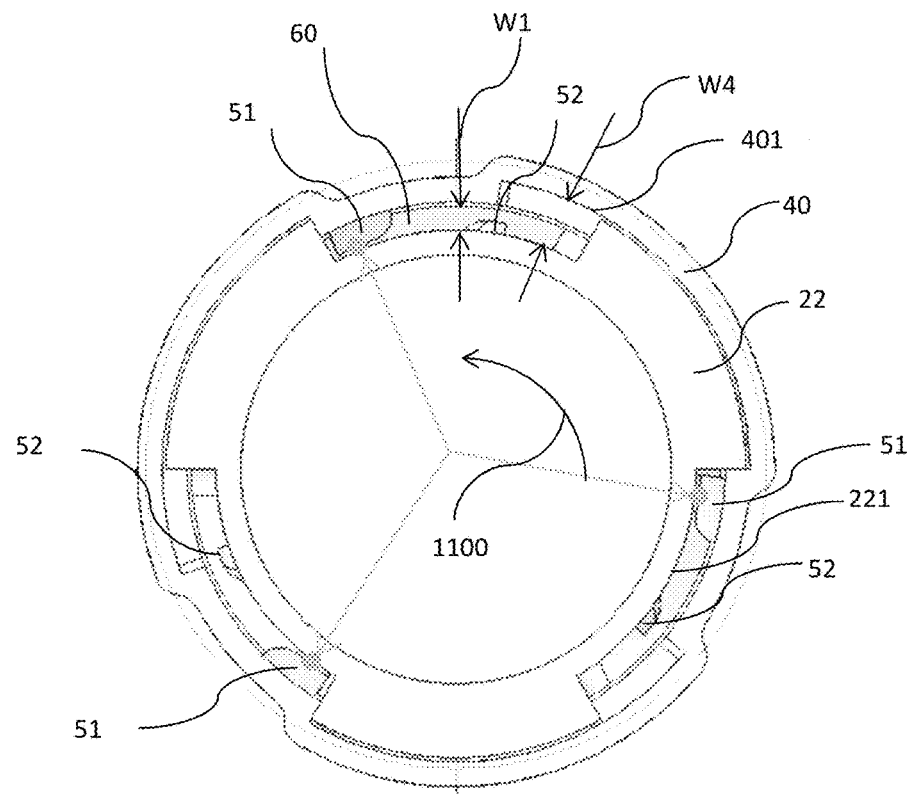
FIG. 15 is a rear view of the button within the rear frame as shown in FIG. 14A.
Figures 16A, 16B:
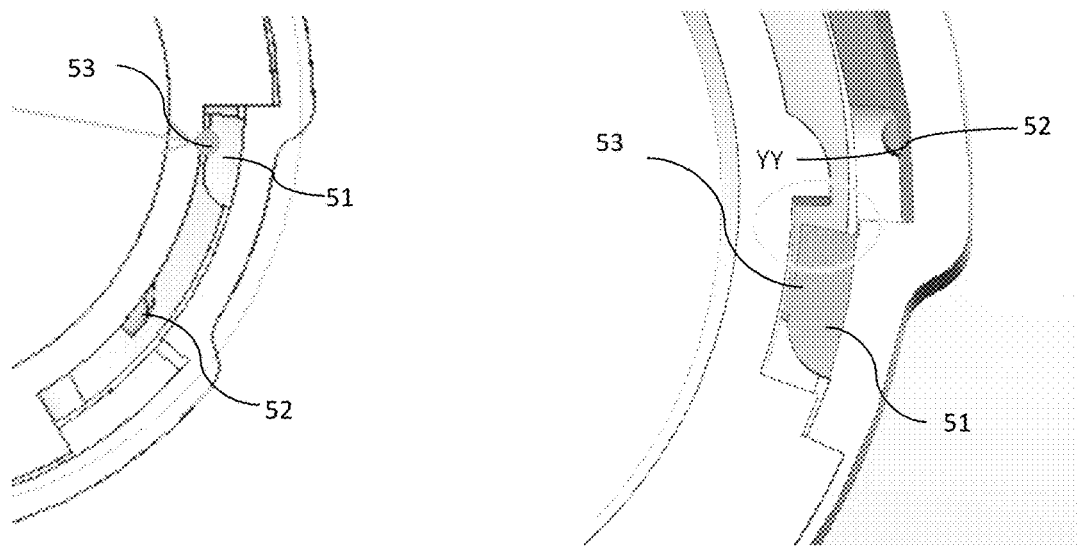
FIG. 16A is a detailed rear view of the button of FIG. 15.
FIG. 16B is a detailed rear view of the button in a second position.

FIG. 15 is an interior section view of the first protrusions 51 and the second protrusions 52 when the button 20 is in the rest position before activation and corresponds to FIG. 14A. FIG. 16A is a detailed view of FIG. 15 and FIG. 16B show the first protrusions 51 and the second protrusions 52 when the button 20 is in the post-activation position after activation. As the button 20 is configured to be axially movable along the longitudinal axis 1000 and rotatable about the longitudinal axis 1000 with respect to the rear frame 200, the first and second protrusions 51, 52 may be radially and axially spaced apart about the longitudinal axis 1000 and arranged within the gap 60 between the button body 22 and the inner wall 40 to allow for locking of the button 20 upon activation.

As shown in FIG. 15, the button body 22 comprises a stepped outer surface 221 configured to mate with a stepped inner surface 401 of the inner wall 40 for slidable movement of the button 20 within the rear frame opening 201 and arranged to form variable gap widths including the first gap width W1 and a second gap width W4 within the gap 60. In the first position as shown in FIG. 15 and FIG. 16A, the second protrusion 52 is radially spaced apart from the first protrusion 51 and is aligned to engage with and move past the first protrusion 51 in a radial direction 1100 about the longitudinal axis 1000.

The number of first protrusions 51 on the inner wall 40 and the number of second protrusions 52 on the button 20 may be equivalent and varied according to a diameter or width of the button body 22. In an example, such as shown in FIG. 15, three first protrusions 51 are disposed on and spaced circumferentially on the inner wall 40 and a corresponding number of second protrusions 52 are disposed on and spaced circumferentially on the button body 22. In an embodiment, the dispenser 1 may further comprise a third protrusion 53 disposed within the gap 60 for preventing free movement of the button 20 in the at rest position. The third protrusion 53 may be integral with the first protrusion 51 as shown in FIG. 15B.

In the embodiments shown, the inner wall 40, the first protrusion 51 and the frame 200 may be molded and form a unitary unit and may comprise plastic for ease of manufacturing. Similarly, the second protrusion 52, the cam guide 80 and the button 20 may also be molded and form a unitary plastic component. Alternatively, the button 20, and the frame 200 and the first and second protrusions 51, 52 may comprise sheet metal, such as spring steel, and may be stamped or milled to form a unitary metal component.

The volatile composition dispenser 1 may comprise a small form factor such as a form factor similar to a computer mouse so as for ergonomic fit in the hand of the user and ease of use. In embodiments, physical specifications of the inner wall 40, the button 20, the first and second protrusion 51, and the cam guide 80 may be configured based on a specified button stroke S (millimeters) and/or a specified rotation angle β (degrees) of the button 20 relative to the longitudinal axis 1000 as shown in FIG. 17B. Referring to FIGS. 12, 13A and 13B, Table 1 sets out physical specifications of the inner wall 40, the button 20, the protrusions 51, 52 and the cam guide 80 based on a button stroke S of 4.25 mm and a rotation angle β of 42.5 degrees. A correlation between a button stroke S and a rotation angle β, S/β may be 0.1 mm/degree.

Therefore, it will be appreciated by a person skilled in the arts that the present invention is not limited to the physical specifications of Table 1. Specifically, the physical specifications may be modified based on a desired button stroke or button rotation angle using the correlation of S/β=0.1 mm/degree. Further, the physical specifications may be modified by using a ratio of the cam angle, α to the button rotation angle, β being 1.3.

TABLE 1

| Symbol as shown in FIGS. 11, 12A, 12B | Button Stroke S = 4.25 mm Button Rotation Angle, β = 42.5 degrees |
|---|---|
| D1 (mm) | — |
| D2 (mm) | 4.63 |
| D3 (mm) | 8.9 |
| D4 (mm) | 9.95 |
| D5 (mm) | 13.85 |
| D6 (mm) | 6.6 |
| Diameter Ø1 (mm) | 14.75 |
| Diameter Ø2 (mm) | 16.27 |
| Diameter Ø3 (mm) | 14.36 |
| Diameter Ø4 (mm) | 17.76 |
| Diameter Ø5 (mm) | 17.15 |
| Diameter Ø6 (mm) | 16.03 |
| Diameter Ø7 (mm) | 14.41 |
| Diameter Ø8 (mm) | 17.34 |
| Diameter Ø9 (mm) | 15.53 |
| Angle α(degrees) | 55.25 |
| Angle γ(degrees) | 77.07 |
| Angle Φ(degrees) | 55.17 |

The internal components of the cartridge 30 as shown in FIG. 3 may be characterized as follows. For example, dimensions of the container 32 may be configured to hold about 1 ml to about 50 ml of a liquid volatile composition. Alternatively, the reservoir 52 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition. Further, a shape of the container 32 may be configured to correspond to a shape of the opening 101 of the front cover 100. For example, the container 32 may define a substantially elliptical or oval shape and its width to length ratio may be about 1:2 to 1:2.5.

The rupturable substrate 33 can be made of any material that ruptures with applied force, with or without the presence of an element to aid in such rupture. Because the rupturable substrate 33 is intended to contain a volatile material while in storage, it may be made from any barrier material that prevents evaporation of the volatile material prior to its intended use. Such materials may be impermeable to vapors and liquids. Suitable barrier materials for the rupturable substrate 33 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 33. Such coated barrier films include metallized PET, metalized polypropylene, silica or alumina coated film may be used. Any barrier material, whether coated or uncoated, may be used alone and or in combination with other barrier materials.

The rupture element 37 can be injection, compression, or pressure molded using a polyolefin, such as polyethylene or polypropylene; polyester; or other plastics known to be suitable for molding. The rupture element 130 could also be made by thermoforming with a discrete cutting step to remove parts not wanted.

The membrane 39 may have an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns. Further, the membrane 39 may be filled with any suitable filler and plasticizer known in the art. Fillers may include finely divided silica, clays, zeolites, carbonates, charcoals, and mixtures thereof. The microporous membrane 39 may be filled with about 50% to about 80%, by total weight, of silica, alternatively about 60% to about 80%, alternatively about 70% to about 80%, alternatively about 70% to about 75%. A thickness of the membrane 39 may be about 0.01 mm to about 1 mm, alternatively between about 0.1 mm to 0.4 mm, alternatively about 0.15 mm to about 0.35 mm, alternatively about 0.25 mm.

Still further, an evaporative surface area of the microporous membrane 39 may be about 2 cm$^2$ to about 100 cm$^2$, alternatively about 2 cm$^2$ to about 25 cm$^2$, alternatively about 10 cm$^2$ to about 50 cm$^2$, alternatively about 10 cm$^2$ to about 45 cm$^2$, alternatively about 10 cm$^2$ to about 35 cm$^2$, alternatively about 15 cm$^2$ to about 40 cm$^2$, alternatively about 15 cm$^2$ to about 35 cm$^2$, alternatively about 20 cm$^2$ to about 35 cm$^2$, alternatively about 30 cm$^2$ to about 35 cm$^2$, alternatively about 35 cm². Accordingly, the rear frame 200 may be sized and shaped to fit the evaporative surface area of the membrane 39.

Suitable microporous membranes for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor®, available from DSM (Netherlands), and Teslin™, available from PPG Industries, and combinations thereof.

A volatile material or composition suitable for use in the cartridge 30 for a volatile composition dispenser 1 may be configured to condition, modify, or otherwise change the atmosphere and may include compositions suitable for the purposes of providing fragrances, air fresheners, deodorizers, odor eliminators, malodor counteractants, insecticides, insect repellants, medicinal substances, disinfectants, sanitizers, mood enhancers, and aromatherapy aids. A list of the suitable volatile materials is shown in Table 2 below.

TABLE 2

| Purpose | Volatile Material |
|---|---|
| Providing fragrances | Perfume oil, volatile essential oils, volatile organic compound, synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. Suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like. |
| Neutralize malodors | Suitable malodor compositions include reactive aldehydes and ionones |

The composition may be formulated such that the composition comprises a volatile material mixture comprising about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. The volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr; and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

An example is shown below:

A. A volatile composition dispenser (1) comprising:
   a) a housing (10) comprising a rear frame (200) wherein the rear frame (200) comprises a frame opening (201) having a longitudinal axis (1000);
   b) an inner wall (40) in the opening (201), the inner wall (40) comprising a proximal end (41) at a periphery (207) of the opening (201) and a distal end (42);
   c) a push button (20) configured to be movable within the frame opening (201) from a first position to a second position relative to the distal end (42) of the inner wall (40), wherein the push button (20) comprises a button body (22);
   d) at least one first protrusion (51) located at the distal end (42) of the inner wall (40);
   e) at least one second protrusion (52) disposed on the button body (22) wherein the second protrusion (52) is aligned to engage with and move past the first protrusion (51) as the button (20) is moved from the first position to the second position; and
   f) a volatile composition cartridge (30) disposed within the housing (10) adjacent the push button (20).

B. The volatile composition dispenser (1) according to paragraph A, further comprising a gap (60) between a base (521) of the second protrusion (52) on the button body (22) and a base (511) of the first protrusion (51) on the inner wall (40), wherein the gap (60) comprises a gap width (W1) less than a sum of a depth (D1) of the first protrusion (51) relative to the inner wall (40) and a depth (D2) of the second protrusion (52) relative to the button body (22).

C. The volatile composition dispenser (1) according to paragraph A, wherein one of the first protrusion (51) and the second protrusion (52) comprises:
   a first surface (512, 522) for engaging the other one of the first protrusion (51) and the second protrusion (52);
   a second surface (513, 523) opposed to the first surface (512, 522);
   wherein an angle (515, 525) of the first surface (512, 522) relative to the inner wall (40) or button body (22) is greater than an angle (516, 526) of the second surface (513, 523) relative to the inner wall (40) or button body (22).

D. The volatile composition dispenser (1) according to paragraph C, wherein the angle (516, 526) of the second surface (513, 523) is greater than 30 degrees and less than or equal to 90 degrees relative to the inner wall (40) or the button body (22).

E. The volatile composition dispenser (1) according to paragraph B, wherein D1 is in the range of 1% to 2% of a width W2 of the inner wall (40).

F. The volatile composition dispenser (1) according to paragraph B, wherein D2 is in the range of 1% to 2% of a width W3 of the button body (22).

G. The volatile composition dispenser (1) according to paragraph A, wherein one of the first protrusion (51) and the second protrusion (52) is a continuous lip extending circumferentially around the inner wall (40) or the button body (22).

H. The volatile composition dispenser (1) according to paragraph A, wherein the button body (22) and the inner wall (40) are substantially cylindrical, and the dispenser comprises:
   a plurality of first protrusions (51) spaced circumferentially on the inner wall (40);
   a plurality of second protrusions (52) spaced circumferentially on the button body (22).

I. The volatile composition dispenser (1) according to paragraph H, wherein at least one of the plurality of first protrusions (51) and second protrusions (52) are generally elongate and extends in a direction parallel to the longitudinal axis (1000) of the frame opening (201).

J. The volatile composition dispenser (1) according to paragraph I, wherein each of the second protrusions

(52) comprise a length (L2) and each of the first protrusions (51) comprises a length (L3), wherein each of L2 and L3 is in the range of 7% to 20% of a length (L4) of the button (20), and L2 is greater than L3.

K. The volatile composition dispenser (1) according to paragraph J, wherein L3 is in the range of 1% to 55% of L2.

L. The volatile composition dispenser (1) according to paragraph A further comprising a cam guide (80) disposed on the button body (22) and at least one protrusion (51) located on the inner wall 40 and aligned with the cam guide (80).

M. The volatile composition dispenser (1) according to paragraph A, wherein the first protrusion (51) and the rear frame (200) form a unitary unit.

N. The volatile composition dispenser (1) according to paragraph A, wherein the second protrusion (52) and the button (20) form a unitary unit.

O. The volatile composition dispenser (1) according to paragraph M or N, wherein the first protrusion (51) and the rear frame (200) or the second protrusion (52) and the button (20) comprise plastic.

P. The volatile composition dispenser (1) according to paragraph A, wherein the second protrusion (52) is disposed on a flexible wall section (25) of the button (20) configured for generating a click sound as the button (20) is moved from the first position to the second position.

Q. The volatile composition dispenser (1) according to paragraph A, further comprising a front cover (100) configured to be attached to the rear frame (200) to form the housing (10) for supporting the cartridge (30).

R. A method of assembling a housing for a volatile composition dispenser, the method comprising:
providing a housing (10) comprising a rear frame (200) and a volatile composition cartridge (30) disposed within the housing (10), wherein the rear frame (200) comprises a frame opening (201) having a longitudinal axis (1000);
providing an inner wall (40) in the opening (201), the inner wall (40) comprising a proximal end (41) and a distal end (42) wherein at least one first protrusion (51) located at the distal end (42) of the inner wall (40);
providing a button (20) within the frame opening (201), wherein the button is movable from a first position to a second position relative to the distal end (42) of the inner wall (40), wherein the button (20) comprises a button body (22), and at least one second protrusion (52) disposed on the button body (22) for engaging the second protrusion (52) on the button body (22) with and moving past the first protrusion (51) on the inner wall (40) upon pressing the button.

S. A method of locking a push button (20) within a housing (10) of a volatile composition dispenser, the method comprising:
providing a housing (10) comprising a rear frame (200) and a volatile composition cartridge (30) disposed within the housing (10), wherein the rear frame (200) comprises a frame opening (201) having a longitudinal axis (1000);
providing an inner wall (40) in the opening (201), the inner wall (40) comprising a proximal end (41) and a distal end (42) wherein at least one first protrusion (51) located at the distal end (42) of the inner wall (40);
moving a push button (20) within the frame opening (201) wherein the button (20) comprises a button body (22) and at least one second protrusion (52) disposed on the button body (22);
engaging the at least one second protrusion (52) disposed on the button body (22) with and moving past the first protrusion (51) on the inner wall (40).

T. The method according to paragraph S, wherein moving the push button (20) comprises axial movement of the push button (20) along the longitudinal axis (1000) and rotation of the button (20) about the longitudinal axis (1000).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:
a) a housing comprising a rear frame wherein the rear frame comprises a frame opening having a longitudinal axis;
b) an inner wall in the opening, the inner wall comprising a proximal end at a periphery of the opening and a distal end;
c) a push button that is axially and rotatably movable within the frame opening from a first position to a second position relative to the distal end of the inner wall in response to a force applied along the longitudinal axis, wherein the push button comprises a button body, wherein the button body and the inner wall are substantially cylindrical;
d) a plurality of first protrusions located at the distal end of the inner wall and spaced circumferentially;
e) a plurality of second protrusions disposed on the button body wherein each of the plurality of second protrusions is aligned to engage with and move past one of the plurality of first protrusions as the button is moved from the first position to the second position; and
f) a volatile composition cartridge disposed within the housing adjacent the push button.

2. The volatile composition dispenser according to claim 1, wherein at least one of the plurality of first protrusions and second protrusions are generally elongate and extends in a direction parallel to the longitudinal axis of the frame opening.

3. The volatile composition dispenser according to claim 2, wherein each of the plurality of second protrusions comprise a length (L2) and each of plurality of first protrusions comprises a length (L3), wherein each of L2 and L3 is in the range of 7% to 20% of a length of the button, and L2 is greater than L3.

4. The volatile composition dispenser according to claim 3, wherein L3 is in the range of 1% to 55% of L2.

5. The volatile composition dispenser according to claim 1 further comprising a cam guide disposed on the button body, wherein the plurality of first protrusions are aligned with the cam guide.

6. The volatile composition dispenser according to claim 1, wherein the plurality of first protrusions and the rear frame form a unitary unit.

7. The volatile composition dispenser according to claim 6, wherein the plurality of first protrusions and the rear frame comprise plastic.

8. The volatile composition dispenser according to claim 1, wherein the plurality of second protrusions and the button form a unitary unit.

9. The volatile composition dispenser according to claim 1, further comprising a front cover configured to be attached to the rear frame to form the housing for supporting the cartridge.

* * * * *